United States Patent [19]

Edgar

[11] 4,320,967
[45] Mar. 23, 1982

[54] APPARATUS FOR MEASURING A RADIATION AFFECTING PARAMETER OF A FILM OR COATING

[75] Inventor: Roger F. Edgar, Maldon, England

[73] Assignee: Infra-Red Engineering Ltd., United Kingdom

[21] Appl. No.: 129,810

[22] Filed: Mar. 12, 1980

[30] Foreign Application Priority Data

Apr. 9, 1979 [GB] United Kingdom ............... 12398/79
Aug. 28, 1979 [GB] United Kingdom ............... 29736/79

[51] Int. Cl.$^3$ ...................... G01N 21/86; G01B 11/06
[52] U.S. Cl. ...................................... 356/51; 250/339; 356/73; 356/382; 356/429
[58] Field of Search ................... 356/73, 51, 418, 429, 356/382; 250/339

[56] References Cited

U.S. PATENT DOCUMENTS

| 3,455,637 | 7/1969 | Howard | 356/429 X |
| 3,793,524 | 2/1974 | Howarth | 356/429 X |
| 3,854,044 | 12/1974 | Stay et al. | 250/339 X |
| 4,027,161 | 5/1977 | Williams et al. | 250/339 |

FOREIGN PATENT DOCUMENTS 2104916  8/1972  Fed. Rep. of Germany ...... 356/429

Primary Examiner—Vincent P. McGraw
Attorney, Agent, or Firm—Steele, Gould & Fried

[57] ABSTRACT

The apparatus employs two or more beams of radiation of different spectral composition which are transmitted through a sample and received by a detector which provides signals for computing the required parameter by ratio measurements. The beams are directed to a sample zone where a part is transmitted through, and a part is reflected by a sample. The invention provides diffusing means to receive the transmitted and reflected parts and pass the same onto a radiation responsive detector. The diffusing means may be a ground glass plate or a member made of fused alumina. A concave mirror may be used to reflect the reflected part back through the sample zone which is close to or at the center of curvature of the mirror. A beamsplitter may also be used so that the beams are directed substantially normal to a plane in the sample zone.

14 Claims, 4 Drawing Figures

APPARATUS FOR MEASURING A RADIATION AFFECTING PARAMETER OF A FILM OR COATING

This invention relates to apparatus for determining the thickness, moisture content, or other parameter of a film or coating capable of transmitting electromagnetic radiation.

U.S. Pat. Nos. 3,089,382 and 3,153,722 describe similar examples of known optical gauging apparatus employing a transmission measurement for the determination of, for example, the thickness or composition of a film or coating. Another example of the technique is the "Infra Gauge" described in Modern Plastics, Volume 44, No. 8, Page 54, August 1967.

The technique customarily used in such apparatus comprises the steps of deriving two or more beams of radiation of different spectral composition, causing them to be transmitted through the sample of material to be measured, collecting by optical means some part of the transmitted radiation and causing it to impinge upon a radiation responsive detector or detectors, demodulating or otherwise processing the output signal or signals from said detector or detectors so as to provide a first set of electrical signals respectively representing the separate intensities of the beams of radiation that have been transmitted through the sample of material to be measured, and of computing the parameter or parameters that are to be determined by forming second set of electrical signals related to the ratios of first electrical signals. The spectral compositions of the beams are chosen so as to provide a differential change in the intensities of the beams as a result of their transmission through the sample of material to be measured with respect to the parameter or parameters to be determined. A beam exhibiting a substantial change in transmitted intensity for a given change in the parameter or parameters to be determined may be described as an absorption beam, while a beam exhibiting a lesser change may be described as a reference beam.

When an apparatus of this type is used to measure a parameter of a thin film or coating (for example, the thickness, moisture content or composition of said film or coating), the precision of the measurement may be degraded by optical interference effects which cause changes in the transmitted intensities of the beam, these changes being not directly related to the variation in the parameter to be measured.

The strength of these optical interference effects is a function of the spectral composition of the several beams of radiation. It is well known that broadening the spectral bandwidth of a beam of radiation reduces its propensity to generate optical interference effects.

Unfortunately, for measurements on certain thin films, the degree of broadening of spectral bandwidth necessary to reduce optical interference errors to acceptably low levels has the secondary effect of reducing the differential change in the transmitted intensities of the several beams to a level at which photometric errors will degrade the precision of the measurement.

U.K. Pat. No. 1,382,081 discloses a technique of combining either transmitted and reflected beams, or the outputs of detectors responsive thereto, to cancel intensity variations due to interference. While this technique considerably improves precision of measurement, the preferred way of carrying it out requires two beams exhibiting interference effects of equal intensity to be accurately aligned with a detector or respective detectors, which alignment becomes more difficult when the two beams follow completely different paths to the same or different detectors. This problem is partly solved, for example, by arranging a specular reflector on one side of a film and a common detector on the other side so that it receives a reflected beam directly from the film surface, and a transmitted beam which has passed twice through the film. However, the most difficult problem to overcome in applying the technique is avoiding misalignment of the film, both in terms of angle and position, since the film may be as much as 4 m. wide and may move at speeds of up to 20 m/sec in a continuous film production plant. U.K. Pat. No. 1,382,081 discloses a roller arrangement to overcome the problem of misalignment with a moving film. However, there is a practical limitation in that it is difficult to maintain the roller surface to a sufficiently high degree of reflectivity and free of organic contamination.

The present invention seeks to solve these problems by providing apparatus for determining or controlling a parameter or parameters which represent the thickness, moisture content, composition or other property of a film or coating capable of transmitting electromagnetic radiation, the apparatus including means for defining a sample zone in which the sample of film or coating can be received; a source of electromagnetic radiation; radiation responsive detector means; optical filter means for deriving a plurality of beams of radiation of differing spectral compositions from said source; first optical directing means for directing said plurality of beams from said source to said sample zone; second optical directing means for directing a part of each of said plurality of beams, which is transmitted by said sample when present, from said sample zone to said radiation responsive detector means; third optical directing means for directing a part of each of said plurality of beams, which is reflected by said sample when present, from said sample zone, to said radiation responsive detector means; means for demodulating or otherwise processing an output signal or signals derived from said radiation responsive detector means so as to provide a first set of electrical signals each representing the respective summed intensity of said transmitted and reflected parts; and means for providing at least one second signal which represents a ratio of at least two of said signals of said first set, characterised in that diffusing means are provided to optically combine said transmitted and reflected parts and to pass the same on to said radiation responsive detector means.

The second signal or signals may be supplied to indicating means to provide a read-out of the parameter or parameters to be measured, or it may be supplied to control means which are operative for example, to maintain said parameter or parameters at a given value.

The radiation responsive detector means may include either separate receivers, or a common receiver for the transmitted and reflected beams.

Preferably a concave mirror is used to reflect that part of said beams which is reflected from the sample (when present) back through said sample zone, the sample zone lying close to, or at the center of curvature of the concave mirror.

It is also preferable to use a normal, or near normal arrangement wherein said beams are first directed through a partly transmissive and partly reflective beam splitter on one side of the sample zone so that said beams are directed substantially normal to a plane in the sample zone which is occupied, in use, by a major surface of the film or coating. A reflector on the other side of the sample zone returns that part of the beams transmitted, in use, through the sample back to the beam splitter. The latter part, together with the reflected part which is also returned to the beam splitter, are then reflected by the beam splitter through the diffusing means and onto the detecting means. The reflector on the other side of the sample zone is advantageously a concave mirror with its centre of curvature at the plane of the sample in the sample zone. This alleviates any problems of, for example, tilting of the plane of a film moving in the sample zone and relaxes the tolerance on alignment of the optical systems on each side of the sample zone.

The diffusing means may be a ground glass plate but it is preferable to use a member made of fused alumina, such as thin sheet or substrate of this substance as provided for use in the manufacture of integrated circuit devices. The substrate should be as thin as possible, consistent with a minimum acceptable physical strength, and is typically 0.5 mm. thick but possibly 0.1 mm. thick.

One of the advantages of the invention, at least in its preferred embodiments, is that the apparatus is more tolerant of angular and positional misalignment of the film than the prior art apparatus. This relaxes the demand on the mechanical arrangements used to maintain a moving film in a given position in the sample zone. A further advantage of using diffusing means is that it provides a substantially even intensity of illumination of the radiation responsive detecting means by the reflected and transmitted parts of the beams. In the prior art, the intensity of reflected beams, in particular, tends to be patchy due to flutter and movement of, for example, a moving film. Another advantage is that the precision of measurement is substantially unaffected by the surface quality of the film and no other arrangement is required as in the prior art. The advantages of the prior art arrangement are also preserved in that measurement is substantially unaffected by optical interference effects, regardless of the thickness of the film, coating or substrate and in that precision does not deteriorate rapidly when the thickness of the film coating or substrate becomes substantially less than the optical coherence length of the several beams of radiation.

Different ways of carrying out the invention are described below with reference to the drawings, in which.

Figure 3:
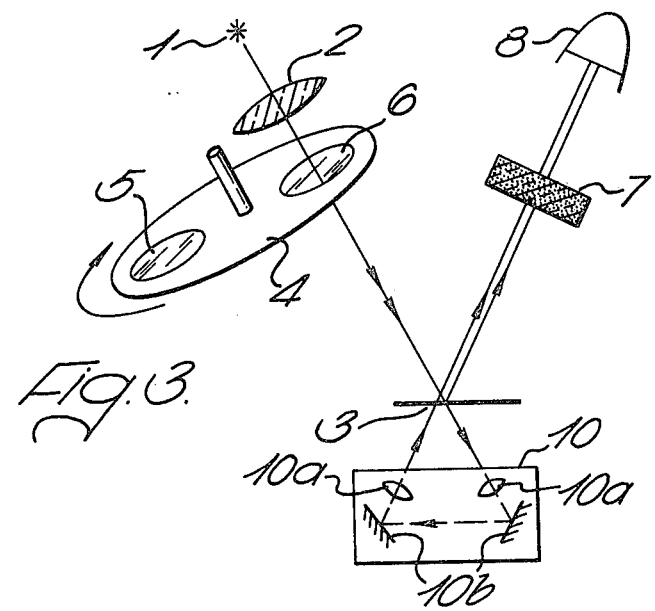
Figure 4:
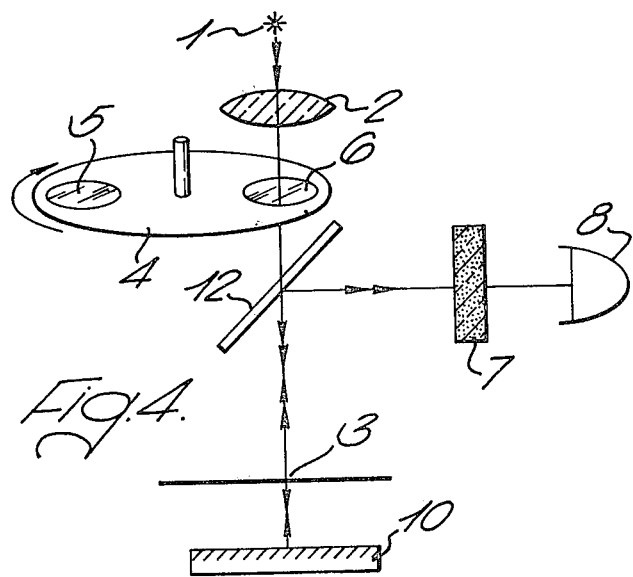

FIG. 3 is a schematic diagram of an apparatus for measuring the thickness, moisture content or other parameter of a film or coating in which the source of electromagnetic radiation and the radiation responsive detector means are located on the same side of the film or coating; and FIG. 4 is a schematic diagram of a similar apparatus in which the path of the electromagnetic radiation from source to detector is at normal incidence to the sample of film.

Hereinafter the term 'light' will be used in place of 'electromagnetic radiation', it being understood that as used 'light' does not imply a restriction to the part of the electromagnetic spectrum to which the eye is sensitive.

Figure 1:
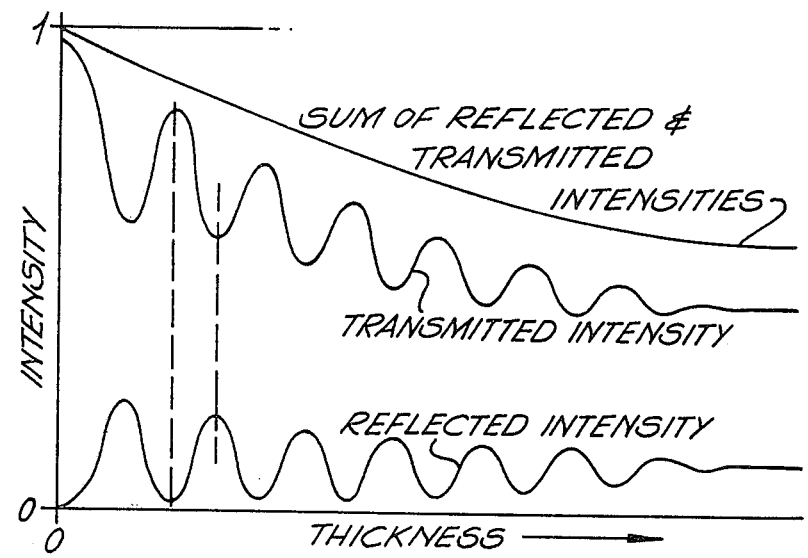
FIG. 1 shows schematically the relationship between the intensities of transmitted and reflected beams and the thickness of the film or coating to be measured.

Referring to FIG. 1, it will be seen that as the thickness of a flat film is reduced, its transmission intensity is no longer a smooth function of thickness but is subject to oscillations which reach a maximum amplitude towards zero thickness. Generally this effect becomes significant once the film or coating thickness is less than half the coherence length of the light used. This condition may be expressed mathematically as $$t \leq \lambda^2/2n\delta\lambda$$

where n is the refractive index of the film or coating, t is its thickness, $\lambda$ is the mean wavelength of the beam of light and $\delta\lambda$ is its bandwidth, (which is customarily defined as the interval between the two wavelengths at which the transmission of the optical filter system has fallen to one half of its peak value). This relationship is an order of magnitude expression and neglects the effect of absorption in the film or coating, but provides a rough guide as to when optical interference effects may be significant.

In FIG. 1 it will be seen that the intensity of the reflection from the film or coating also ceases to be a smooth function as thickness is reduced. Further, it will be seen that the maxima in reflected intensity occur at the same thicknesses as the minima in transmitted intensity and vice versa. Thus, if the transmitted and reflected beams are combined, the effect of optical interference is substantially eliminated, leaving the desired absorption effect to be measured. The three embodiments described below incorporate alternative means of combining the intensities of each pair of transmitted and reflected beams.

Figure 2:
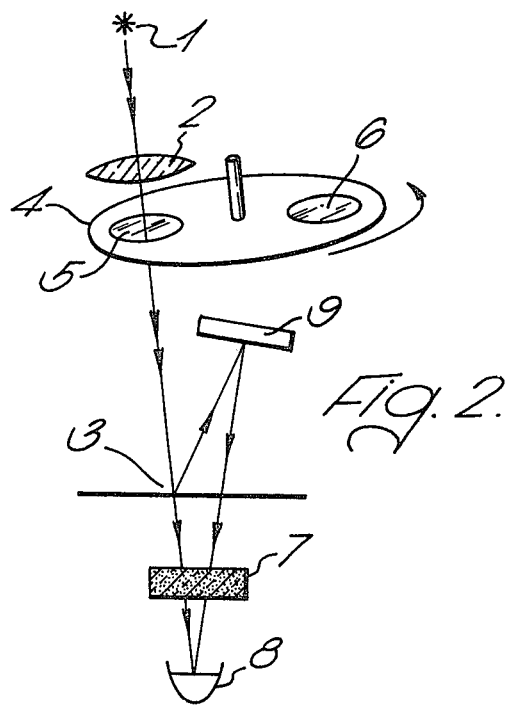
FIG. 2 is a schematic diagram of an apparatus for measuring the thickness, moisture content or other parameter of a film or coating in which the source of electromagnetic radiation and the radiation responsive detector means are on opposite sides of the film or coating.

In FIG. 2, light from a source 1 is directed by an optical system 2 onto the sample of film or coating 3 by way of a rotating wheel 4 which carries optical filters 5 and 6. The light selected by the optical filters 5 and 6 and transmitted by the film or coating 3 then passes through diffusing means 7, such as a ground glass plate to a radiation responsive detector 8. The radiation reflected by the film or coating 3 is directed by another optical system 9, through the film, and is then directed by diffusing means 7 onto the detector 8.

The criteria for the selection of optical filters 5 and 6 and the use of more than the two filters shown here are known in the prior art and will not be discussed further here. Likewise, the usual steps of amplification, demodulation and subsequent processing of the detector output signal are known in the prior art and will not be discussed further here.

The optical system 2 is conveniently a lens, but a simple aperture can be used instead to define the direction of the beams.

By using diffusing means, such as a ground glass plate 7, to diffuse the light onto the detector 8, good tolerance is provided to misalignment of the components of the apparatus on opposite sides of the film or coating.

The optical system 9 can conveniently be a prism, mirror or other reflector. If the optical system 9 comprises a plane mirror it is placed close to the film or coating.

A more useful embodiment uses a concave mirror as the optical system 9. This mirror is positioned so that the sample of film or coating 3 lies close to its center of curvature.

It can be demonstrated that such an optical system is tolerant of angular misalignment or position variations of the sample 3, relaxing the demand on the mechanical arrangements used to maintain the position of the sample.

In FIG. 2, the beam of radiation is shown passing through the sample of film or coating 3 at a non-normal angle so that the optical system 9 does not obstruct the beam of light incident upon the sample 3.

It is frequently preferable to make the measurement with the beam passing normally through sample 3. In this case the optical system 9 would obstruct the incident beam. The solution to this difficulty is to make the optical system 9 substantially reflective, but also slightly transmissive over a sufficient area as to permit the passage of the incident beam to the sample 3. A reflective efficiency of at least 80 percent is necessary if the ability of the system to eliminate interference effects is not to be impaired. A normal, or near normal arrangement is described below with reference to FIG. 4.

In the embodiment of FIG. 3, light from a source 1 is directed by an optical system 2 onto the sample of film of coating 3 by way of a rotating wheel 4 which carried optical filters 5 and 6. The light transmitted by the sample 3 is directed by a third optical system 10, which forms an image of the film back upon itself (as does a concave mirror 9 in the FIG. 2 embodiment), so as to be incident upon sample 3 a second time, and the light which is transmitted on the second interaction is passed by diffusing means, such as a ground glass plate 7, onto radiation responsive detector 8. Light is reflected from the sample 3 into the diffusing means 7 by two primary routes. The first route is by simple reflection from sample 3; the second is by successive transmission reflection and transmission by sample 3. (It will be apparent that a small amount of light may follow other paths, involving several reflections at the sample 3, but this is not material to an understanding of the apparatus).

The optical system 2 is conveniently a lens. The optical system 10 can include two lenses 10a and two mirrors 10b, or an alternative system giving the same effect. The lens 2 may sometimes be dispensed with and a simple aperture relied on to define the direction of the beams.

In FIG. 4 is shown an embodiment which offers the advantage of a light beam at normal incidence to the sample of film. Light from source 1 is directed by an optical system 2 onto the sample of film or coating by way of a rotating wheel 4 which carries optical filters 5 and 6, and by way of a semi-transparent beamsplitter 12. The light transmitted by the sample 3 is directed by the optical system 10 so as to be incident upon sample 3 a second time, and a part of the light which is transmitted on the second interaction is reflected by beamsplitter 12, and directed by diffusing means, such as a ground glass plate 7, onto a radiation responsive detector 8. Light is reflected from the sample 3 and enters the plate 7 by two primary routes.

The first route is by reflection from sample 3 followed by reflection at beamsplitter 12; the second is by successive transmission, reflection and transmission by sample 3, followed by reflection at beamsplitter 12. Optical system 2 can be conveniently be a lens and optical system 10 a plane mirror close to sample 3 or a concave mirror with its center of curvature in the plane of the film. In the case of using a concave mirror 10, an image of the film is formed back on itself. This relaxes the tolerance on alignment of the optical systems on each side of the film.

The apparatus described above with reference to FIGS. 2, 3 and 4 operates by using diffusing means to combine the beams simultaneously derived by transmission and reflection and directing them jointly to a common detector.

In the embodiments described above with reference to FIGS. 2 to 4, the apparatus has been described utilising optical configurations in which the beams of differing spectral composition are derived by the use of optical filters set into a rotating wheel. Alternative means of deriving the beams using prisms, diffraction gratings etcetera will be clear to persons skilled in the art.

It will also be clear to persons skilled in the art that the precise location of the optical filter means in the radiation path from the source to the detector is not critical, provided of course that both transmitted and reflected beams are subject to an identical filtering process.

It will also be clear to persons skilled in the art that the invention is not restricted to optical gauging apparatus in which a radiation responsive detector receives beams of differing spectral compositions sequentially in time, but may apply equally to such apparatus in which a radiation responsive detector simultaneously receives beams of differing spectral composition modulated with differing carrier frequencies.

Likewise the use of the invention in optical guaging apparatus in which a different radiation responsive detector is used for each of the beams of differing spectral composition may be seen to be straightforward.

What is claimed is:

1. An apparatus for determining or controlling at least one parameter which represents at least one property of a film or coating capable of transmitting electromagnetic radiation, comprising:
   means for defining a sample zone in which a sample of the film or coating can be received;
   a source of electromagnetic radiation;
   radiation responsive detector means;
   optical filter means for deriving a plurality of beams of radiation of differing spectral compositions from said source;
   optical directing means so arranged that:
      (a) said plurality of beams are directed from said source to said sample zone;
      (b) a part of each of said plurality of beams, which is transmitted by said sample when present, is directed from said sample zone to said radiation responsive detector means; and,
      (c) a part of each of said plurality of beams, which is reflected by said sample when present, is directed from said sample zone to said radiation responsive detector means;
   diffusing means for optically combining said transmitted and reflected parts and passing said combined parts onto said radiation responsive detector means;
   means for processing at least one output signal derived from said radiation responsive detector means so as to provide a first set of electrical signals each representing the respective summed intensity of said effective transmitted and reflected beams; and,
   means for providing at least one second signal which represents a ratio of at least two of said signals of said first set.

2. The apparatus according to claim 1, wherein said diffusing means comprises a ground glass plate.

3. The apparatus according to claim 1, wherein said diffusing means is a member made of fused alumina.

4. The apparatus according to claims 1, 2 or 3, wherein said optical means comprises a concave mirror for reflecting said reflected part back through said sample zone, said sample zone lying close to the center of curvature of the concave mirror.

5. The apparatus according to claims 1, 2 or 3, wherein said optical means comprises a partly transmissive and partly reflective beam splitter on one side of said sample zone so that said beams are directed substantially normal to a plane in the sample zone which is occupied, in use, by a major surface of the film or coating; and, a reflector disposed on the other side of said sample zone to return said transmitted part, through the sample zone, to the beam splitter.

6. The apparatus according to claim 5, wherein the reflector disposed on the other side of said sample zone is a concave mirror having a center of curvature in the plane which, in use, is occupied by a sample in the sample zone.

7. The apparatus according to claim 4, wherein said sample zone lies at the center of curvature of the concave mirror.

8. The apparatus according to claim 1, wherein the optical directing means is further so arranged that the reflected part passes through the sample zone not more than once, and the transmitted part passes through the sample zone not more than twice, prior to entering the diffusing means, whereby the sample zone is defined by not more than one point of reflection and not more than two points of transmission.

9. The apparatus according to claims 1 or 8, wherein the source of electromagnetic radiation and the diffusing means are disposed on opposite sides of the sample zone, and the optical means comprises a reflector for directing the reflected part back through the sample zone, the reflected part passing through the sample only once, and the transmitted part passing through the sample only once, prior to entering the diffusing means, whereby only two beams enter the diffuser and are optically combined and subsequently processed.

10. The apparatus according to claims 1 or 8, wherein the source of electromagnetic radiation and the diffusing means are on the same side of the sample zone, and the optical means comprises a reflector for directing the transmitted part back through the sample zone, the transmitted part passing through the sample only twice and the reflected part not passing through the sample at all, prior to entering the diffusing means, whereby only two beams enter the diffuser and are optically combined and subsequently processed.

11. The apparatus according to claim 9, wherein the reflector is a concave mirror.

12. The apparatus according to claim 10, wherein the reflector is a concave mirror.

13. The apparatus according to claim 10, wherein the reflector comprises two reflective surfaces and two focusing elements.

14. The apparatus according to claim 10, wherein the optical means further comprises a beam splitter operationally disposed between the source of electromagnetic radiation and the sample zone, between the source of electromagnetic radiation and the diffusing means and between the sample zone and the diffusing means.

* * * * *